United States Patent [19]

Hansen

[11] 3,987,665

[45] Oct. 25, 1976

[54] NON-DESTRUCTIVE TEST METHOD FOR ASSESSING TEXTILE MATERIAL DEGRADATION

[75] Inventor: John V. E. Hansen, Westboro, Mass.

[73] Assignee: The United States of America as represented by the Secretary of the Army, Washington, D.C.

[22] Filed: Aug. 22, 1975

[21] Appl. No.: 606,820

[52] U.S. Cl. .................................. 73/67.2; 73/159
[51] Int. Cl.² ................. G01N 29/00; G01N 33/36
[58] Field of Search ............................ 73/67.2, 159

[56] References Cited
UNITED STATES PATENTS

| 2,178,252 | 10/1939 | Forster | 73/67.2 |
| 2,744,408 | 5/1956 | Seney | 73/67.2 |
| 3,319,460 | 5/1967 | Barigant | 73/67.2 |
| 3,394,587 | 7/1968 | Freeman | 73/67.2 X |

Primary Examiner—James J. Gill
Attorney, Agent, or Firm—Nathan Edelberg; Robert P. Gibson; Lawrence E. Labadini

[57] ABSTRACT

Method for determining, non-destructively, degradation of certain physical properties of textile materials wherein a sample of the textile material is held under tension and caused to ring to generate acoustic signals and the frequency of the acoustic signal is compared with the frequency generated from a control of the same material, with any significant difference in frequency of response of the sample as compared with the control indicating a change in physical property.

10 Claims, No Drawings

NON-DESTRUCTIVE TEST METHOD FOR ASSESSING TEXTILE MATERIAL DEGRADATION

The invention described herein may be manufactured, used, and licensed by or for the Government for governmental purposes without the payment to me of any royalty thereon.

BACKGROUND OF THE INVENTION

This invention relates to a test method for determining whether a textile material has experienced any significant degradation in certain physical properties and, more particularly, to a non-destructive test method to assess whether textile materials have experienced any significant loss in material strength.

Textile fabrics, yarns and fibers, both synthetic and natural, are known to experience degradation in their physical properties as a consequence of various environmental events or conditions. Where such textile materials are used in applications involving critical dependence upon the original strength of the material, a need exists to evaluate such materials following suspected degradation of that property. Presently, such textile materials may be discarded after a given period of time (in use or in storage) which historical experience has shown to be within the limits of safety or acceptability. Such procedure is not absolutely reliable in terms of safety and may, on the other hand, be exceedingly wasteful in that the materials may, in fact, be acceptable for a much longer period of time or use due to its special environmental history and experience. Alternatively, a statistical sample of a textile material may be tested to destruction and the results used in making a decision with respect to the acceptability of the sample lot. Such a procedure is obviously faulty in that each item is not tested and while the sample may pass inspection, individual items within the lot might fall with disastrous consequences. Further, any destructive tests, in the case of expensive or complex items, will necessarily result in the loss or destruction of that item which can, in fact, be a serious economic loss.

Degradation of textile materials can result from chemical attack, such as exposure to acids, bases, oxidizing and reducing agents, microbiological attack by bacteria or fungi which utilize enzymes to hydrolyze polymer chains, physical agents such as ultraviolet radiation, and other effects such as loss of plasticizer, changes in crystalline state and order which occur naturally with time or under conditions of use. The effects of such degradative changes can be negligible in the case of some agents and some textile materials, or so extensive as to completely destroy the strength of the material.

The complexity of the degradative processes on different textile materials indicates that to be valid, a test procedure must be sensitive to the overall mechanical state or physical condition of the material rather than to merely one particular condition. A non-destructive test that could assess the physical condition of the material quickly and inexpensively would do much to insure the safety or reliability of the material or system dependent thereon as well as result in savings in both energy and materials.

A specific instance of the use of a textile material in a life-critical situation occurs in connection with personnel parachutes. Such parachutes are made of woven nylon canopies, nylon fabric risers and harnesses. Parachute nylon will predictably be degraded and suffer a loss in physical strength upon exposure to ultraviolet radiation over a period of time, with the ultraviolet radiation producing a molecular reordering in the polymer molecule due to scission within the molecule. In addition, exposure to elevated temperatures is known to degrade the physical properties of these same nylon materials. As indicated above, the only present test which will determine the physical strength of these parachute materials is a destructive test which destroys the parachute component.

The object of this invention is to provide a non-destructive test that may be employed to establish any deviation in physical strength of a textile material from that of its original or normal state.

SUMMARY OF THE INVENTION

A test method, which is non-destructive, for determining any deviation from the standard or normal condition of the textile material. This method requires placing a length of the sample textile material under tension, impacting said tensioned material to produce acoustic signals representing the natural frequency and determining the frequency of those acoustic waves or signals. The frequency of these acoustic signals is compared to the frequency of a control of the same material known not to have been degraded with any deviation in the frequency of the test material being indicative of a degradation of that material.

DESCRIPTION OF THE PREFERRED EMBODIMENT

In the practice of this invention, advantage is taken of the fact that materials which are relatively flexible, elastic and capable of elongation, i.e., capable of deformation along its axis under a tensile stress, when placed under a given tension, can be caused to vibrate to produce acoustic signals representing the natural frequency. These acoustic signals or sound waves can be detected and analyzed to ascertain the frequency of the signals. This invention is based upon the discovery that aside from changes in natural frequency of the acoustic signals that can be effected by merely changing the tension in a given material, a change in the physical state or physical strength of the material will also effect or alter the frequency of the vibratory response.

Textile materials, as that term is used herein, is intended to encompass single fibers, filaments, yarns and woven fabrics which can be made to vibrate under tension to produce an acoustic signal which can be detected. Such materials may be composed of natural or synthetic polymers or blends or mixtures of the same. Staple fibers and filaments can be tested according to this procedure either individually or as components of yarns and fabrics.

Test material is tensioned or stressed along the fiber or yarn axis and in the case of fabrics, along one of the main axes (warp or filling). The extent of the tension applied may vary with the nature of the material and with the weave of the fabric; but it is necessary that the tension be sufficient so that the material will, under a suitable impact, generate a detectable acoustic signal.

Such acoustic signals may be detected by any conventional acoustic sensing device, such as a microphone which converts the energy of the acoustic signals to electrical signals. These electrical signals may be transmitted to an oscilloscope which graphically displays the time-amplitude wave form traces of the vibrations. The wave form traces on the oscilloscope can be permanently recorded photographically and analyzed to determine the frequency of the vibrations. The electrical signals may alternatively be transmitted to a frequency analyzer which will directly read out the frequency of the acoustic signals.

The following illustrative example discloses in detail the operation of the process of this invention.

EXAMPLE

In this example, nylon ripstop fabric (1.1 oz) samples measuring 4 × 12 inches were cut from a single piece of fabric. This fabric is further described in military specification MIL-C-7020 for Cloth, Parachute, Nylon. The short end of one fabric sample was inserted in the jaws of a 4.125 inch jaw clamp which clamp was mounted on a support stand. The opposite short end of the fabric was fastened to a second jaw clamp of the same size, weighing approximately 5.18 lbs. and allowed to hang free in a vertical orientation from the first clamp. The second jaw clamp provided a constant moderate tension on the sample (approximately 1.25 lbs. per inch width) which tension is in a unidirection, i.e., along one of the fiber or weave axes. The center of the fabric sample while under tension was struck a sharp blow with an impactor (a hard rubber cylinder), causing it to ring in its free or resonant modes generating acoustical waves. A microphone of conventional design, placed behind the sample, converted the acoustical signals to electrical signals which were routed to an oscilloscope displaying the time-amplitude trace of the signals. The trace was photographically recorded and the frequency of the wave form was determined to be 90 hz. A second identical fabric sample was exposed for 34 hours to ultraviolet radiation from a carbon arc source. This exposure resulted in a 30–34% loss in physical strength. This sample was then tested as above and the frequency of the acoustic signal generated thereby was 70 hz. From this and other tests with this fabric, it has been established that a downward shift in the frequency of the acoustic signals occurs when this fabric is degraded, i.e., experiences a reduction in tensile or physical strength.

It is noted that altering the tension or stress applied to samples of textile materials will alter the frequency of response but that if samples of the same kinds of material are tensioned to the same extent, any significant variation in acoustical frequency response is due to some alteration in the physical properties of the material caused by a molecular reordering within the structure.

The invention described in detail in the foregoing specification is susceptible to changes and modifications as may occur to persons skilled in the art without departing from the principle and spirit thereof. Terminology used is for purpose of description and not limitation, the scope of the invention being defined in the claims.

I claim:

1. A non-destructive test method for detecting degradation of physical properties in textile materials which comprises:
   a. placing a fixed length of a test sample of a textile material selected from the group consisting of fibers, yarns and fabrics, under tension,
   b. impacting said tensioned textile material to cause it to ring in its free or resonant mode generating acoustic signals.
   c. detecting the generated acoustic signals,
   d. determining the frequency of the acoustic signals, and
   e. comparing said frequency with the frequency obtained under identical conditions of a non-degraded control of the same textile material, with any deviation from the frequency of the control signifying degradation of physical properties in the test material.

2. A non-destructive test method according to claim 1 wherein the textile material is a fiber.

3. A non-destructive test method according to claim 2 wherein the fiber is tensioned along the fiber axis.

4. A non-destructive test method according to claim 1 wherein the textile material is a yarn.

5. A non-destructive test method according to claim 4 wherein the yarn is tensioned along the yarn axis.

6. A non-destructive test method according to claim 1 wherein the textile material is a woven fabric.

7. A non-destructive test method according to claim 6 wherein the fabric is tensioned along one of its axes.

8. A non-destructive test method according to claim 7 wherein the stress applied to the tensioned fabric is about 1.25 lbs. per inch width.

9. A non-destructive test method according to claim 1 wherein the acoustic signals are detected by a microphone.

10. A non-destructive test method according to claim 1 wherein degradation in textile materials refers to a loss of tensile strength and wherein the acoustic signals are detected by an acoustic sensing device.

* * * * *